US006984719B1

(12) United States Patent
Chemtob et al.

(10) Patent No.: US 6,984,719 B1
(45) Date of Patent: Jan. 10, 2006

(54) PEPTIDE ANTAGONISTS OF PROSTAGLANDIN F2α RECEPTOR

(75) Inventors: Sylvain Chemtob, Montreal (CA); Krishna G. Peri, Montreal (CA)

(73) Assignee: Hospital Sainte-Justine, Montreal (CA)

( * ) Notice: Subject to any disclaimer, the term of this patent is extended or adjusted under 35 U.S.C. 154(b) by 0 days.

(21) Appl. No.: 09/787,334

(22) PCT Filed: Sep. 15, 1999

(86) PCT No.: PCT/CA99/00844

§ 371 (c)(1),
(2), (4) Date: Jun. 19, 2001

(87) PCT Pub. No.: WO00/17348

PCT Pub. Date: Mar. 30, 2000

Related U.S. Application Data

(63) Continuation-in-part of application No. 09/154,627, filed on Sep. 17, 1998.

(51) Int. Cl.
| | |
|---|---|
| A61K 38/04 | (2006.01) |
| A61K 38/00 | (2006.01) |
| C07K 16/00 | (2006.01) |
| C07K 14/00 | (2006.01) |
| A01N 37/18 | (2006.01) |

(52) U.S. Cl. .................. 530/328; 530/300; 530/329; 530/333; 514/2
(58) Field of Classification Search ............. 530/300, 530/328, 329, 333; 514/2; 435/7.2
See application file for complete search history.

(56) References Cited

U.S. PATENT DOCUMENTS

| | | | |
|---|---|---|---|
| 3,691,016 A | 9/1972 | Patel | |
| 3,969,287 A | 7/1976 | Jaworek et al. | |
| 4,195,128 A | 3/1980 | Hildebrand et al. | |
| 4,229,537 A | 10/1980 | Hodgins et al. | |
| 4,247,642 A | 1/1981 | Hirohara et al. | |
| 4,330,440 A | 5/1982 | Ayers et al. | |
| 4,522,752 A | 6/1985 | Sisto et al. | |
| 5,508,384 A | 4/1996 | Murphy et al. | |
| 5,688,938 A | 11/1997 | Brown et al. | |
| 5,955,575 A | 9/1999 | Peri et al. | |

FOREIGN PATENT DOCUMENTS

| | | |
|---|---|---|
| EP | 0 045665 | 9/1985 |
| WO | WO 93/09104 | 5/1993 |
| WO | WO 95/00551 | 1/1995 |
| WO | WO 96/23225 | 8/1996 |

OTHER PUBLICATIONS

Rehwald M. et al. FEBS Letters. 43:357-362, 1999.*
Lake S. et al. FEBS Letters 355:317-325, 1994.*
Kitanaka et al. "Phloretin as an Anatagonist of Prostaglandin $F_{2\alpha}$ Receptor in Cultured Rat Astrocytes", *Journal of Neurochemistry*, vol. 60. No. 2, pp. 704-708, 1993.

Sugimoto et al. "Failure of Parturition in Mice Lacking the Prostaglandin F Receptor", *Science* vol. 277, pp. 681-683, Aug. 1997.

Griffin et al. "AL-8810: A Novel Prostaglandin $F_{2\alpha}$ Analog with Selective Antagonist Effects at the Prostaglandin $F_{2\alpha}$ (FP) Receptor", *The Journal of Pharmacology and Experimental Therapeutics* vol. 290 No. 3, pp. 1278-1284, 1999.

Abramovitz et al. "Cloning and Expression of a cDNA for the Human Prostanoid FP Receptor*", *Journal of Biol. Chem.*, vol. 269, No. 4, pp. 2632-2636, Jan. 28, 1994.

Abran et al. "Regulation of Prostanoid vasomotor effects and receptors in choroidal vessels of newborn pigs" *Amercian Physiologial Society*, pp. R995-R1001, 1997.

Berridge et al. "Changes in the levels of inositol phosphates after agonist-dependent hydrolysis of membrane phosphoinositides" *Biochem. J.*, vol. 212, pp. 473-482 (1983).

Coleman et al. "VIII. International Union of Pharmacology Classification of Prostanoid Receptors: Properties, Distribution, and Structure of the Receptors and Their Subtypes", *Pharmacological Reviews*, vol. 46 No. 2, pp. 205-229 (1994).

Goetzl et al. "Specificity of expression and effects of eicosanoid mediators in normal physiology and human diseases", *The FASEB Journal*, vol. 9, pp. 1051-1058, Aug. 1995.

Li et al. "Inhibition of Prostaglandin Synthesis in Newborn Pigs Increases Cerebral Microvessel Prostaglandin $F_{2\alpha}$ and Prostaglandin $E_2$ Receptors, Their Second Messengers and Vasoconstrictor Response to Adult Levels", *The Journal of Pharmacology and Experimental Therapeutics*, vol. 278, No. 1, pp. 370-377 (1996).

(Continued)

*Primary Examiner*—Robert S. Landsman
(74) *Attorney, Agent, or Firm*—Morgan & Finnegan, L.L.P.

(57) ABSTRACT

The present invention relates to a new class of G protein-coupled receptor agonist or antagonist, which specifically binds to the receptor protein structural elements, thus altering signal transmission and subsequent physiological effects. Described herein are peptide sequences derived from the G protein-coupled receptor protein, produced by chemical methods as selective inhibitors of signal transduction associated with stimulation of the receptor by its ligand. Such peptides or molecules derived from their primary, secondary or tertiary structures may be used as effective tocolytics for the prevention of premature labor or be used for the treatment of dysmenorrhea.

6 Claims, 5 Drawing Sheets

OTHER PUBLICATIONS

Li et al. "Key role for cyclooxygenase-2 in $PGE_2$ and $PGF_{2\alpha}$ receptor regulation and cerebral blood flow of the newbor" *The American Physiological Society*, pp. R1283-R1290 (1997).

Potvin et al. "Refractoriness of the gravid rat uterus to tocolytic and biochemical effects of atrail natriuretic peptide" *Br. J. Pharmacol.*, vol. 100, pp. 341-347 (1990).

Strader et al. "Structure and Function of G Protein-Coupled Receptors" *Annu. Rev. Biochem.* 63:101-32 (1994).

Varma et al. "Endothelium- and Beta-2 Adrenoceptor-Independent Relaxation of Rat Aorta by Tyramine and Certain Other Phenylethylamines" *The Journal of Pharmacology and Experimental Therapeutics*, vol. 265, No. 3, pp. 1096-1104 (1993).

Almquist et al., *J. Med. Chem.* 23:1392-1398 (1980).

Baldwin, J. M., et al., *J. Mol Biol.* 272:144-164 (1997).

Crankshaw D. J., *Biology of Reproduction* 46, pp. 392-400 (1992).

Crankshaw D. J., *Can J Physiol Pharmacol* 72, pp. 870-874 (1994).

Goodman et al. *Perspectives in Peptide Chemistry* pp. 283-294 (1981).

Hann, J. *Chem. Soc. Perkin Trans. I* 307-314 (1982).

Hebert, T. E. et al., *J. Biol Chem.* 271:16384-92 (1996).

Holladay et al., *Tetrahedron Lett.* 24:4401-4404 (1983).

Hruby, *Life Sci.* 31:189-199 (1982).

Hudson et al., *Int. J. Rept. Prot. Res.* 14:177-185 (1979).

James, G. L. et al. *Science* 260:1937-1942 (1993).

Jennings-White et al., *Tetrahedron Lett.* 23:2533 (1982).

Lofts et al. *Oncogene*, 8:2813-2820 (1993).

Morley J. S., *Trends Pharm. Sci.* pp. 463-468 (1980).

Powell A. M, *Prostaglandins*, vol. 29, No. 2, pp. 273-289 (1985).

Senior J et al., *Br J Pharmacol*, 107, pp.215-221 (1992).

Spatola et al., Life Sci. 38:1243-1249 (1986).

Spatola, in *Chemistry and Biochemistry of Amino Acids, Peptides and Proteins*, Weinstein, ed., Marcel Dekker, New York, p. 267 (1983).

Taylor, J. M. et al., *Cell Signal* 6:841-9 (1994).

Unger V.M., et al., *Nature* 389:203-206 (1997).

\* cited by examiner

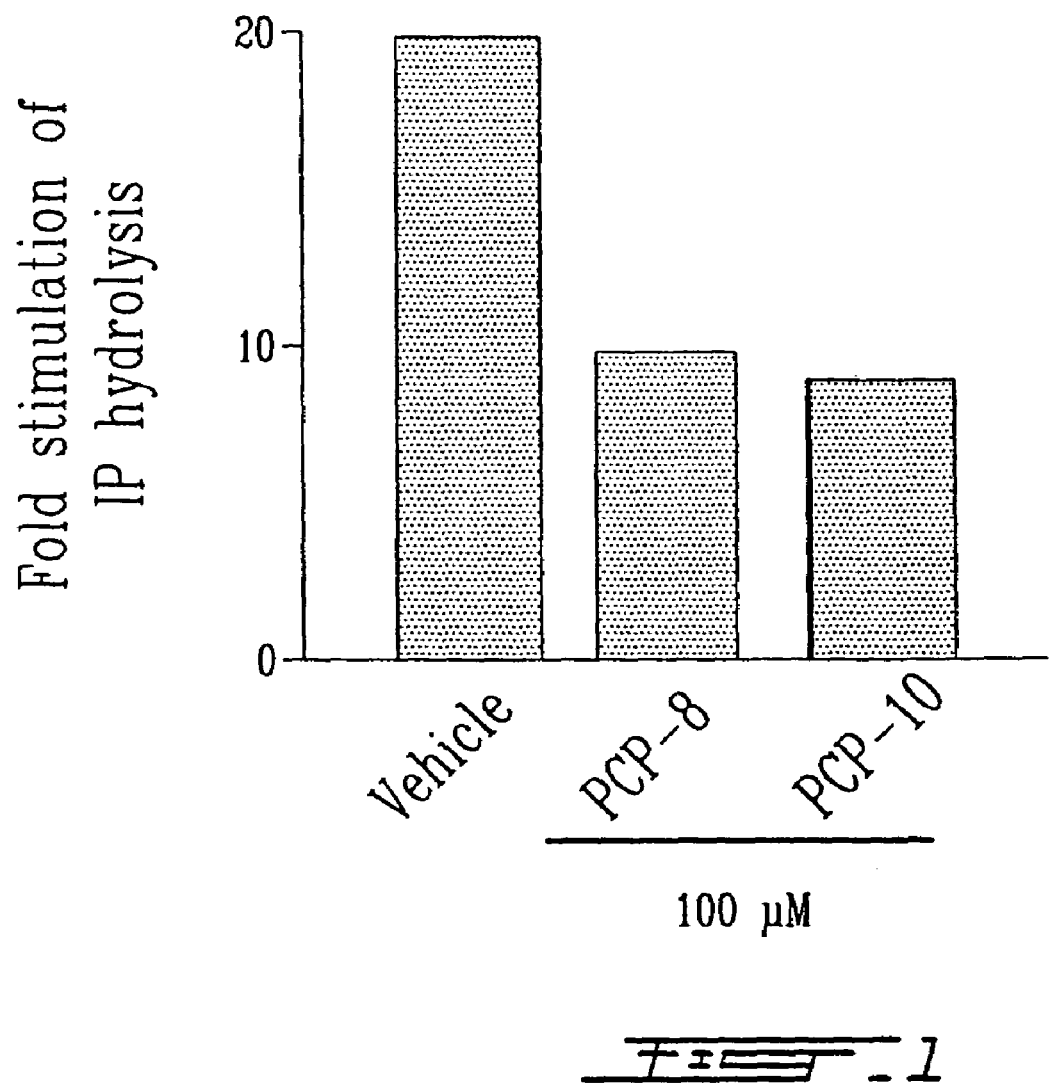

FIG. 2a

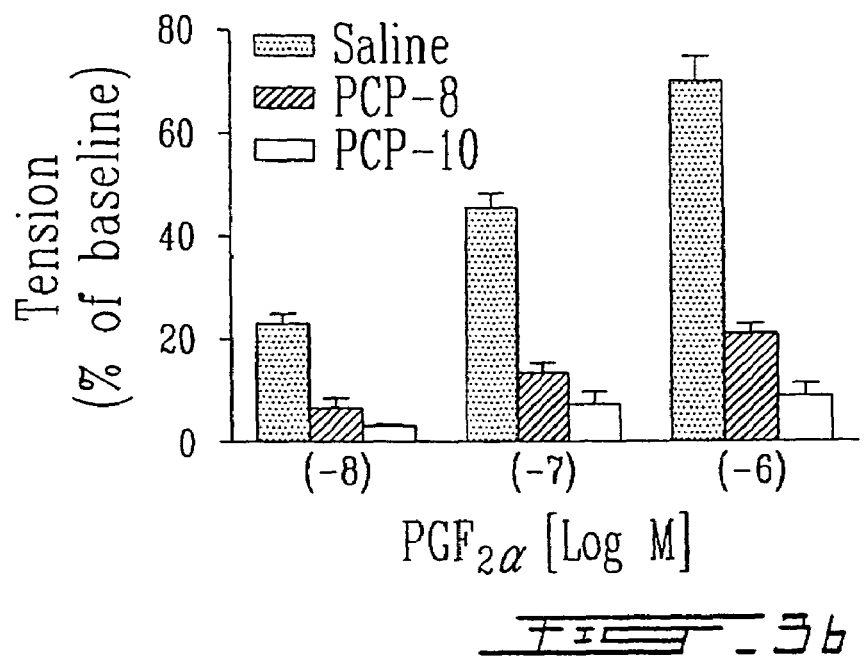
_FIG_3b_
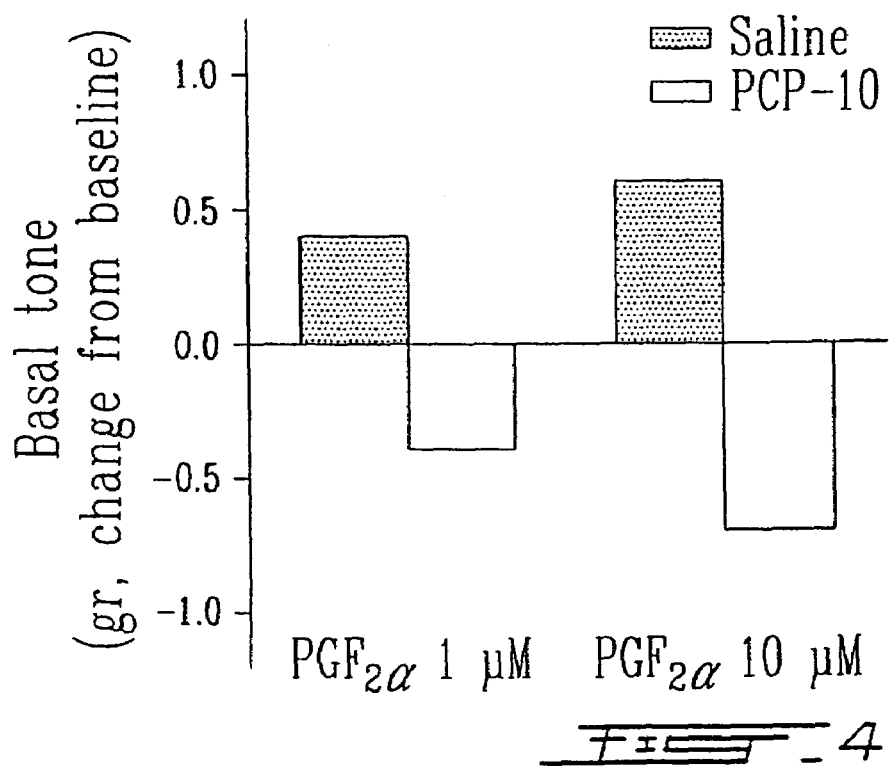
_FIG_4_

PEPTIDE ANTAGONISTS OF PROSTAGLANDIN F2α RECEPTOR

This application is the national stage of International Application PCT/CA99/00844 which claims priority to and is a continuation-in-part of U.S. application Ser. No. 09/154,627 (now abandoned).

BACKGROUND OF THE INVENTION (a) Field of the Invention

The invention relates to development of agonist or antagonist of a G protein-coupled receptor, which bind to the G protein-coupled receptor from the extra-cellular side in a manner different from that of the natural ligand.

(b) Description of Prior Art

Prostaglandins are derived from the oxygenation of arachidonic acid by prostaglandin synthetases. Prostaglandins mediate a wide variety of physiological actions, such as vasomotricity, sleep/wake cycle, intestinal secretion, lipolysis, glomelular filtration, mast cell degranulation, neurotransmission, platelet aggregation, leuteolysis, myometrial contraction and labor, inflammation and arthritis, patent ductus arteriosus, cell growth and differentiation (Coleman, R. A. et al., 1994, *Pharmacol. Rev.* 46:205–229; Goetzl, E. J. et al., 1995, *FASEB J.* 9:1051–10585). Prostanoids mediate their actions through binding to distinct receptors, which belong to the super family of rhodopsin-like seven transmembrane helical receptors. These receptors are coupled to heterotrimeric G-proteins comprising of α, β and γ subunits which, upon activation, elicit alterations in cell calcium, initiate phosphoinositide hydrolysis or promotion or repression of cyclic adenosine monophosphate synthesis (Strader C. D. et al., 1994, *Ann. Rev. Biochem.* 63:101–132).

Of the five pharmacologically distinct prostanoid receptors for $PGE_2$, $PGI_2$, $PGD_2$, $PGF_{2\alpha}$ and $TxA_2$ and their many isoforms, the receptor for $PGF_{2\alpha}$, also called FP receptor, shows limited tissue distribution, predominantly expressed in corpora leutea, uterine myometrium, trabecular meshwork of the eye, and to a lesser extent in vascular smooth muscle. Initiation of labor is marked by tremendous rise in $PGF_{2\alpha}$ levels and increased uterine contractility. The wide spread use of $PGF_{2\alpha}$ analogues to induce labor in veterinary industry points to the primary role of $PGF_{2\alpha}$ and its receptor in parturition. This is underscored by the fact that mice lacking the FP receptor fail to undergo labor (Sugimoto et al., 1997, *Science* 277:81–83). In face of escalating costs incurred as a result of premature births and associated complications to the neonate, such as intraventricular hemorrhage, bronchopulmonary displasia and periventricular leukomalacia leading to cerebral palsy, prolongation of gestation by arresting premature labor is an effective preventive therapy. The relative success of nonsteroidal anti-inflammatory drugs as a short-term therapy toward prevention of premature labor is based on their inhibitory actions upon the synthesis of prostaglandins, particularly $PGE_2$ and $PGF_{2\alpha}$. However, inhibition of $PGE_2$ is associated with serious complications to the fetus such as the closure of ductus arteriosus, renal failure and pulmonary hypertension.

At another level, $PGF_{2\alpha}$ has been attributed a major role in dysmenorrhea, a condition which afflicts 5%–7% of premenopausal women. A pre-menstrual increase in $PGF_{2\alpha}$ levels resulting in myometrial spasms underlies the pathogenesis of this disorder. Lack of effective antagonists of FP receptor for extended therapy hampered the advances in preventing premature labor and associated sequelae, and the design of such antagonists is the subject of this application.

Human FP receptor is a 45 kDa integral membrane glycoprotein, consisting of 359 amino acids and shares only 47% sequence identity with $EP_1$ receptor, and to a lesser extent with other prostanoid receptors (Abramovitz et al., 1994, *J. Biol. Chem.* 269:2632–2636). Binding of $PGF_{2\alpha}$ to FP receptor is followed by the activation of $G_{\alpha q \beta \gamma}$ complex, increased GTP binding by the $G_{\alpha q}$ subunit, stimulation of phospholipase Cβ activity, release of inositol phosphates, increased intracellular calcium and subsequent signal transduction phenomena ultimately leading to smooth muscle contraction (Coleman, R. A. et al., 1994, *Pharmacol. Rev.* 46:205–229). The FP receptor is the only efficacious target for development of therapeutic drugs since a few $G_\alpha$-proteins catalyze the actions of hundreds of G-protein coupled receptors, thus targets downstream from the receptor are essentially of little use.

Antagonists of FP receptors directed to the ligand binding site could be of limited use since ligand based inhibitors show cross reactivity with other prostanoid receptors. Their efficacy will be compromised in face of tremendous increase in $PGF_{2\alpha}$ concentrations in myometrium at the onset of labor and in menstruation. The high basal activity of the receptors in the absence of ligand limits the use of ligand-based inhibitors.

It would be highly desirable to be provided with agonist or antagonist of FP receptors, which do not crossreact with other prostanoid receptors, and are effective even in the presence of excess ligand.

SUMMARY OF THE INVENTION

One aim of the present invention is to provide agonist or antagonist of FP receptors, which do not crossreact with other prostanoid receptors.

Another aim of the present invention is to provide activators or inhibitors of FP receptors by a novel strategy to target the extracellular domains of the receptor protein.

In accordance with the present invention, there is provided a G protein-coupled receptor agonist or antagonist which specifically binds to the juxtamembrane extracellular structural elements of the G protein-coupled receptor in a manner different from that of the natural ligand, and wherein said agonist or antagonist alter the transduction of an intracellular signal. The G protein-coupled receptor agonist or antagonist may be derived from the amino acid sequence of the receptor.

In accordance with a preferred embodiment of the present invention, the agonist or antagonist does not crossreact with other prostanoid receptors.

The antagonist is effective in the presence of excess ligand.

The agonist or antagonist may preferably comprise an amino acid sequence derived from the first and/or second extracellular loops of prostanoid receptors.

In accordance with another embodiment of the present invention, the antagonists of the present invention comprise amino acid sequences derived from the first and second extracellular loops of prostanoid receptors.

In accordance with a preferred embodiment of the present invention, the G protein-coupled receptor is the prostaglandin $F_{2\alpha}$ receptor (FP receptor).

In accordance with a preferred embodiment of the present invention, the antagonist of the present invention comprises amino acid sequences derived from the prostaglandin $F_{2\alpha}$ receptor.

Preferably, the antagonist include, without limitation, amino acid sequence of the FP receptor selected from the group consisting of ilghrdyk (PCP-8; SEQ ID NO:1); wedrfyll (PCP-10; SEQ ID NO:2); YQDRFYLL (PCP-14; SEQ ID NO:3); ILAHRDYK (PCP-13.7; SEQ ID NO:4); ILGFRDYK (PCP-13.11; SEQ ID NO:5); ILGHKDYK (PCP-13.13; SEQ ID NO:6); ILGHRNYK (PCP-13.14; SEQ ID NO:7); ILGHQDYK (PCP-13.18; SEQ ID NO:8); ILGHRDY-amide (PCP-13.20; SEQ ID NO:9); ILGH-RDYK-amide (PCP-13.21; SEQ ID NO:15); ILGWRDYK (PCP-13.22; SEQ ID NO:10); ILGXRDYK (PCP-13.24; SEQ ID NO:11); SNVLCSIF (PCP-15; SEQ ID NO:12) protein fusions and peptidomimetics thereof; wherein said amino acid sequence contains L- and/or D-amino acid.

In accordance with the present invention, there is provided a peptide having an amino acid sequence selected from the group consisting of SEQ ID NO:1 to 15 and wherein said amino acid sequence contains L- and/or D-amino acid, an amino acid sequence with at least about 90% homology to SEQ ID NO: 1 to 15, and peptidomimetic thereof.

In accordance with the present invention, there is provided a pharmaceutical composition containing at least a G protein-coupled receptor agonist and antagonist of the present invention, mixture thereof, or functional derivatives thereof in association with a pharmaceutically acceptable carrier.

In accordance with another embodiment of the present invention, there is provided a method for preventing premature delivery of fetus, which comprises the step of administering to a female in need of such a treatment a therapeutically effective amount of a G protein-coupled receptor antagonist or functional derivatives thereof, wherein the antagonist or functional derivatives thereof specifically binds to the extracellular face of the receptor, thereby hampering uterine contractions.

In accordance with another embodiment of the present invention, there is provided a method for pre-venting and/or treating dysmenorrhea comprising the step of administering to a female in need of such a treatment a therapeutically effective amount of a G protein-coupled receptor antagonist or functional derivatives thereof, wherein the antagonist or functional derivatives thereof specifically binds to the extracellular face of the receptor to hamper transduction of a signal thereby reducing the pain associated with contractions.

In accordance with another embodiment of the present invention, there is provided a method of identifying a compound as a G protein-coupled receptor agonist or antagonist capable of binding to the extracellular elements of the said receptor in a manner different from that of the natural ligand, comprising the steps of:
  a) culturing cells which express said receptor or identifying animal tissues ex vivo or in vivo where physiological consequences are dependent on said receptor;
  b) contacting said cells or tissues with said compound to be tested for agonist or antagonist activity at said receptor; and
  c) measuring a response to alter the transduction of a signal resulting in physiological consequences selected from the group consisting of increments in cell calcium, phosphoinositide hydrolysis, increased/decreased cellular cyclic adenosine monophosphate, cell growth and/or differentiation, altered gene expression, and smooth muscle contraction or dilation, wherein said response is indicative of agonist or antagonist activity.

In accordance with another embodiment of the present invention, there is provided a method of identifying a compound as a prostaglandin $F_2$ alpha receptor agonist or antagonist capable of binding to the extracellular elements of the said receptor in a manner different from that of the natural ligand, comprising the steps of:
  a) culturing cells which express said receptor or identifying animal tissues ex vivo or in vivo where physiological consequences are dependent on said receptor;
  b) contacting said cells or tissues with said compound to be tested for agonist or antagonist activity at said receptor; and
  c) measuring a response to alter the transduction of a signal resulting in physiological consequences selected from the group consisting of increments in cell calcium, phosphoinositide hydrolysis, cell growth and/or differentiation, altered gene expression, and smooth muscle contraction or dilation, wherein said response is indicative of agonist or antagonist activity. For the purpose of the present invention the following terms are defined below.

In accordance with another embodiment of the present invention, there is provided a prostaglandin F2 receptor antagonist consisting essentially of an amino acid sequence derived from the second extracellular loop of a prostaglandin F2 receptor, said amino acid sequence comprising one or more sequences selected from the group consisting of: ilghrdyk (PCP-8; SEQ ID NO:1); ILGHRDYK (PCP-13; SEQ ID NO:13); ILAHRDYK (PCP-13.7; SEQ ID NO:4); ILGFRDYK (PCP-13.11; SEQ ID NO:5); ILGHKDYK (PCP-13.13; SEQ ID NO:6); ILGHRNYK (PCP-13.14; SEQ ID NO:7); ILGHQDYK (PCP-13.18; SEQ ID NO:8); ILGHRDY-amide (PCP-13.20; SEQ ID NO:9); ILGH-RDYK-amide (PCP-13.21; —SEQ ID NO:15); ILG-WRDYK (PCP-13.22; SEQ ID NO:10); ILaHRDYK (PCP-13.8; SEQ ID NO:14) and ILGXRDYK (PCP-13.24; SEQ ID NO:11), wherein X is cyclohexyl alanine, and wherein small letters indicate L-amino acids and capital letters indicate D-amino acids.

In accordance with another embodiment of the present invention, there is provided a peptide consisting essentially of a variant sequence of any one of SEQ ID NOs:1, 4 to 11, 13, 14 or 15 in which one or more amino acid residues are substituted or deleted, and wherein said variant sequence contains L- and/or D-amino acids and wherein said peptide is a prostaglandin F2 receptor antagonist.

The expression "a G protein-coupled receptor agonist or antagonist" is intended to mean any natural or synthetic compound, peptide protein, antibody, peptidomimetic or small chemical molecules, without limitation, insofar as it can specifically bind to the extracellular structural elements of the G protein-coupled receptor to alter transduction of a signal. More preferably, the agonist or antagonist does not crossreact with other prostanoid receptors.

The expression "functional derivatives" of G protein-coupled receptor agonist or antagonist is intended to mean mimetic compounds and/or structurally unrelated compounds with respect to G protein-coupled receptor antagonist, which can also specifically bind to the extracellular structural elements of the G protein-coupled receptor to alter transduction of a signal.

The expression "peptidomimetic thereof" is intended to mean any chemical entities, mimetic compounds and/or structurally unrelated compounds with respect to G protein-coupled receptor agonist or antagonist, which can also specifically bind to the extracellular structural elements of the G protein-coupled receptor to alter transduction of a signal.

BRIEF DESCRIPTION OF THE DRAWINGS

FIG. 1 illustrates the inhibitory effects of PCP-8 and PCP-10 on FP receptor function upon stimulation with $PGF_{2\alpha}$ in accordance with the embodiment of the present invention;

FIG. 2A illustrates the effects of saline and PCP-10 on the diameter of the microvessels of pig retina upon stimulation with either $PGF_{2\alpha}$ or thromboxane $A_2$ mimetic, U46619;

FIG. 3B illustrates the dose response of prostaglandin $F_{2\alpha}$ in the presence/absence of PCP-8 and PCP-10 upon uterine smooth muscle contraction; and FIG. 4 illustrates the reversal of basal, tone of bovine myometrium even in the presence of FP receptor ligand, $PGF_{2\alpha}$.

DETAILED DESCRIPTION OF THE INVENTION

Figure 2B:
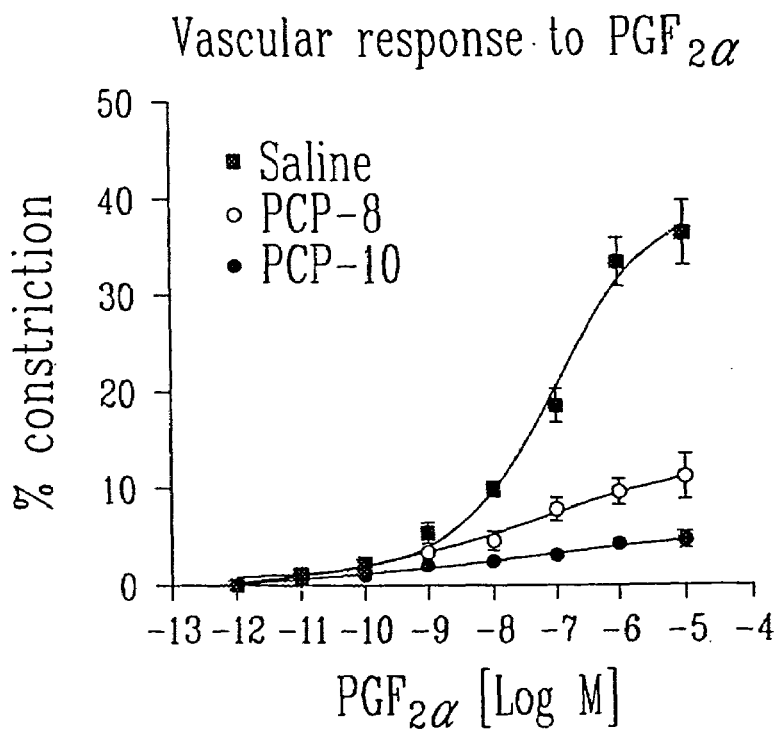
FIG. 2B illustrates the dose response of $PGF_{2\alpha}$ on the diameter of pig microvessels treated previously with PCP-8 or PCP-10.

In accordance with the present invention, there is provided a new class of G protein-coupled receptor antagonists, which bind to the extracellular molecular surface, thus hamper signal transduction.

Also provided is a novel strategy to target the extracellular loops of the receptor which contribute to the structural or functional integrity of the receptor. Antagonists thus bind to cognate elements in the extracellular surface of the receptor and prevent the receptor function by interfering with its signal initiation or transduction.

There is provided proof of selectivity of the antagonists to FP receptor by showing an absence of their effects on a related prostanoid receptor for thromboxane $A_2$, known as TP receptor which is also involved in smooth muscle contraction.

Preparation of Inhibitors

Chemical synthesis of PCP-8 and PCP-10

All peptides which are 8 amino acids in length were synthesized using F-moc chemistry and solid phase Merrifield method two peptides, PCP-8 and PCP-10. These peptides were purified by HPLC and their purity tested by mass spectroscopy.

In accordance with the present invention, a novel strategy of using peptides derived from the extracellular domains of prostaglandin $F_{2\alpha}$ receptor, FP, to inhibit the signal transduction and the functional consequences of FP receptor. This method could be generalized to all G protein-coupled receptors. Peptides derived from the first and second extracellular loops of FP receptor were found to be effective inhibitors of FP receptor.

The present invention could be readily understood by referring to the following examples, which are given to illustrate the invention rather than to limit its scope.

EXAMPLE I

Effects of Peptides, PCP-8 and PCP-10, on Ligand-Induced Phosphoinositide Hydrolysis in Mammalian Cells Overexpressing the FP Receptor Both PCP-8 and -10 were tested in HEK293 cells expressing the human FP receptor. For this purpose, HEK 293 cells stably expressing human FP receptor were plated in 12-well plates in DMEM medium containing 10% fetal bovine serum, penicillin (10 U/ml) and streptomycin (10 µg/ml) and cultured in a humidified atmosphere containing 5% $CO_2$ at 37° C. After the wells were 80% confluent, the cells were labeled with 2 µCi/ml of [$^3$H]-myo inositol overnight. Next day, the cells were washed once with PBS, and incubated in 0.5 ml of Kreb's buffer containing 10 mM LiCl and indicated concentrations of PCP peptides for 30 min. $PGF_{2\alpha}$ at 1 µM was added to the cells and the incubation was carried out for an additional 30 min. The cells were solubilized with 0.1 N NaOH for 10 min and neutralized with 0.1 N formic acid. The lysates were collected and 1 ml each of methanol and chloroform were sequentially added and vortexed briefly. After centrifugation to separate the phases, inositol phosphates were separated by ion exchange chromatography as described below (Berridge, M. J. et al., 1983, Biochem. J. 212:473–482).

Briefly, the medium was discarded and the IP3 synthesis was stopped by adding 0.6 ml ice-cold methanol. The cells were scraped and collected into polypropylene tubes. Distilled water (0.5 ml) and chloroform (0.6 ml) were added and vigorously vortexed for 2 min. The phases were separated by centrifugation at 6000×g for 10 min. The aqueous phase was applied to AG-1X-8™ (Formate form) anion exchange columns (1 ml bed volume) and free inositol was eluted with 10 ml of water, followed by 60 mM ammonium formate in 0.1 M formic acid. Then, the inositol phosphates were eluted with 5 ml of 1.2 M ammonium formate in 0.1 M formic acid. After adding 3 volumes of scintillation cocktail (Optiphase-HiSafe III), the eluates were counted by scintillation spectrophotometry.

The results of these experiments are shown in FIG. 1. Data are expressed as fold stimulation of inositol phosphate synthesis by 1 µM $PGF_{2\alpha}$ compared to the unstimulated controls. Both PCP-8 and -10 at 100 µM potently inhibited inositol phosphate synthesis initiated by the action of $PGF_{2\alpha}$ on FP receptor. The half maximal inhibitory concentrations for both PCP-8 and -10 were slightly less than 100 µM.

EXAMPLE II

Testing PCP Peptides in Porcine Eyecup Model of Ex Vivo Vasomotricity Assay

In order to see if the peptides could inhibit FP function using an ex vivo model, we chose porcine eyecup model, an ex vivo assay of vascular constriction in porcine retinas which we previously described and validated (Li et al., 1996 J. Pharmacol. Expt. Therapeut. 278: 370–377; Li et al., 1997 Am. J. Physiol. 273: R1283–90; Abran et al., 1997 Am. J. Physiol. 272: R995–1001). Since FP receptor densities in newborn vasculature are minimal due to down regulation by high levels of circulating prostaglandins in the perinatal period, the newborn pigs were treated with a prostaglandin synthetase blocker, ibuprofen (30 mg/Kg of bodyweight/8 h for 24 h) to increase the density of the receptors as well as their vasomotor effects. By inhibiting circulating prostaglandins, we were able to show potent inhibition of FP receptor-mediated second messenger synthesis as well as FP-mediated vascular constriction in this eyecup model.

To prepare eyecups, a circular incision was made 3–4 mm posterior to ora serrata to remove the interior segment and vitreous body with minimal handling of the retina. The remaining eyecup was fixed with pins to a wax base in a 20 ml tissue bath containing 20 ml of Kreb's buffer (pH 7.35–7.45), protease inhibitors, leupetin and aprotinin (10 µg/ml each), and equilibrated with 21% oxygen and 5% carbon dioxide at 37° C. The preparations were allowed to stabilize for 30 min. Peptides at 100 µM were added and incubation was continued for 30 min before the addition of $PGF_{2\alpha}$.

Cumulative concentration-responses of $PGF_{2\alpha}$, and $TxA_2$ mimetic, U46619, ($10^{-10}$ to $10^{-5}$ M) curves were constructed separately. To assess the reversibility of the antagonists, the eyecups were thoroughly washed (which would wash away the peptide) with incubation medium and concentration response curves for $PGF_{2\alpha}$ were determined. The outer vessel diameter was recorded with a video camera mounted on a dissecting microscope (Zeiss M 400™) and the responses were quantified by a digital image analyzer (Sigma Scan Software, Jandel Scientific, Corte Madera, Calif.). Vascular diameter was recorded before and 10 min following the topical application of the agent. Each measurement was repeated three times and showed <1% variability.

Figure 2C:
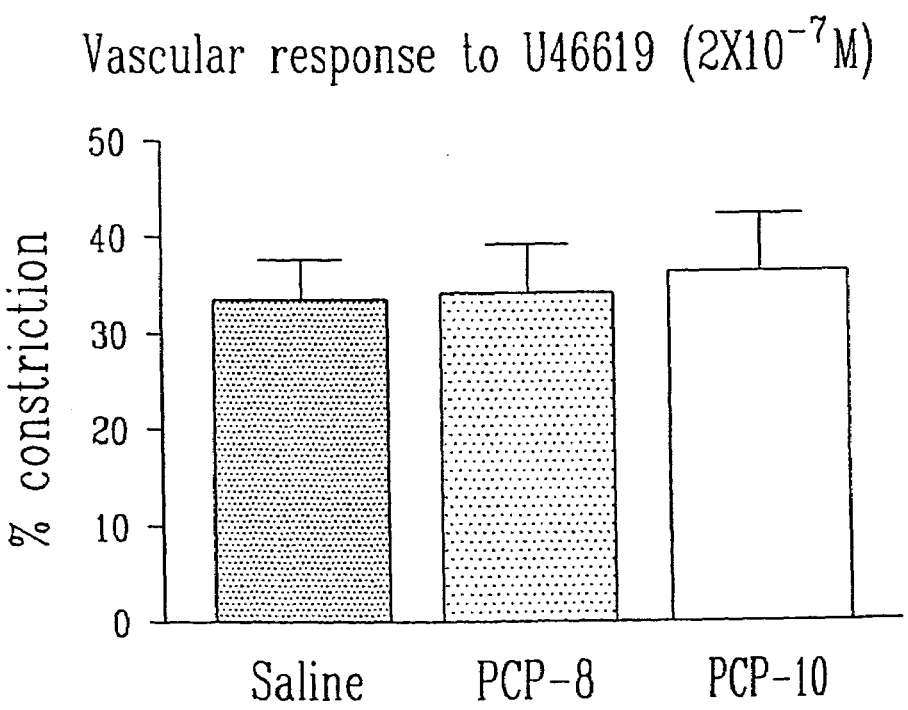
FIG. 2C illustrates the effects of thromboxane $A_2$ mimetic, U46619, on the diameter of pig microvessels treated previously with PCP-8 and PCP-10.

The results are shown in FIG. 2. The peptide PCP-10 had no effect on the basal tone (diameter of the microvessel) of the vessel (FIG. 2A; left panels). Addition of 1 µM of $PGF_{2\alpha}$ potently constricted the vessel in the absence of the peptide (middle-top panel), whereas presence of PCP-10 at 100 µM markedly inhibited $PGF_{2\alpha}$-mediated vasoconstriction (middle-bottom panel). The peptide had no effect on the vasoconstriction effected by 1 µM $TxA_2$ mimetic, U46619, (right panels) acting on another prostanoid receptor coupled to constriction, namely TP receptor. Similar results were obtained for PCP-8 as well. A dose response of $PGF_{2\alpha}$ on the vascular diameter in the presence/absence of PCP-8 and PCP-10 peptides are presented in FIG. 2B. Both peptides abrogated the vasomotor responses even at concentrations exceeding 1 µM of $PGF_{2\alpha}$, suggesting, as expected, that the peptides may be acting in a non-competitive fashion. However, the peptides had no effect on vasoconstriction produced by thromboxane $A_2$ (FIG. 2C).

Similarly, a peptide derived from the first extracellular loop of FP receptor, PCP-15, inhibited $PGF_{2\alpha}$-induced constriction ($10^{-7}$ M) (88.1% over untreated control; Table 1).

EXAMPLE III

Testing Peptide Variants of PCP-8 in Porcine Eyecup Model of Ex Vivo Vasomotricity Assay In order to understand the structural requirements of PCP-8 in its inhibitory action on $PGF_{2\alpha}$-induced vasoconstriction, different amino acids in PCP-8 sequence were replaced with other D- or L-amino acids and the resulting peptides were chemically synthesized and tested in porcine eyecup model of ex vivo vasomotricity assay. These peptide variants are listed in Table 1.

Table 1

Amino Acid Sequences of Peptide Variants of PCP-8 and their Inhibitory Potency in Porcine Eyecup Model Of Ex Vivo Vasomotricity Assay

| Peptide PCP- | % Vasomotor response (of max constriction)[1] | % inhibition of maximal response | Peptide sequence | SEQ ID NO: |
|---|---|---|---|---|
| 8 | 50.0 | 50.0 | ilghrdyk | 1 |
| 10 | 20.0 | 80.0 | wedrfyll | 2 |
| 14 | 36.0 | 64.0 | YQDRFYLL | 3 |
| 13 | 20.0 | 80.0 | ILGHRDYK | 13 |
| 13.7 | 23.8 | 76.2 | ILAHRDYK | 4 |
| 13.8 | 46.8 | 53.2 | ILaHRDYK | 14 |
| 13.11 | 13.0 | 87.0 | ILGFRDYK | 5 |
| 13.13 | 36.9 | 63.1 | ILGHKDYK | 6 |
| 13.14 | 40.3 | 59.7 | ILGHRNYK | 7 |
| 13.18 | 30.0 | 70.0 | ILGHQDYK | 8 |
| 13.20 | 49.6 | 50.4 | ILGHRDY-amide | 9 |
| 13.21 | 46.2 | 53.8 | ILGHRDYK-amide | 15 |
| 13.22 | 16.6 | 83.4 | ILGWRDYK | 10 |
| 13.24 | 6.2 | 93.8 | ILGXRDYK | 11 |
| 15 | 11.9 | 88.1 | SNVLCSIF | 12 |

[1]Percent vasomotor response in the presence of 100 µM peptide is calculated as percent change in average vascular diameter produced by $10^{-7}$ M $PGF_{2\alpha}$ to the eyecup in the presence of the peptide compared to maximal constriction observed in the absence of the peptide.

[2]Percent inhibition produced by each peptide is calculated as (100-percent vasomotor response).

Small letters indicate L-amino acids and capital letters indicate D-amino acids. I=isoleucine; L= leucine; G=glycine; H=histidine; R=Arginine; D=Aspartic acid; Y=Tyrosine; K=Lysine; A=Alanine; W= Tryptophan; E=Glutamic acid; F=Phenyl alanine; Q=Glutamine; N=Aspargine; P=Proline; S=Serine; X=Cyclohexyl alanine. Peptides were dissolved in DMSO freshly just before the experiment as 10 mM stocks and added to the eye cups 30 min before the addition of $10^{-7}$ M $PGF_{2\alpha}$.

A total of 25 variants of PCP-8 were synthesized and the efficacious or potent peptides are listed in Table 1. These peptides incorporate L- to D-amino acid changes, deletions, subtle variations in aromaticity, hydrogen bond donor status as opposed to ionic interactions and hydrophobicity. These peptides were tested at 100 µM concentration in porcine retinal vasomotricity assay and the results are summarized in Table 1.

The results are summarized as follows:
1. Converting all L-amino acids of PCP-8 to D-amino acids (PCP-13) increased the inhibitory potency dramatically. Removal of N-terminal hydrophobic dipeptide sequence from either PCP-8 (PCP-11) or PCP-10 (PCP-12) resulted in significant reduction in the inhibitory action of the peptides.
2. Glycine to alanine (13.7) does not change the activity of PCP-13, whereas change to proline (13.16), L-alanine (13.8), or deletion of the residue (13.17) entirely resulted in loss of activity. Glycine is an important linker residue separating the HRD motif from the IL hydrophobic sequence.
3. HRD-motif is important for the activity of PCP-13. Alanine substitutions (13.1–13.3) or to change to L-configuration (13.4–13.6) resulted loss of inhibitory activity of PCP-13. Aromaticity of His is more important than the positive charge, since H to F (13.11) or W (13.22) or X (13.24), but not to Y (13.23), did not result in significant reduction of peptide inhibitory potency. Side chain length appears to be more critical in case of D residue than R; changing D to E (13.12) resulted in loss of half of the inhibitory activity whereas R to K (13.13) or to Q (13.18) affected the activity of PCP-13 moderately. D to N (13.14) resulted in moderate loss of activity, whereas a serine substitution (13.19) lead to drastic loss of activity of PCP-13.

4. Deletion of terminal lysine (13.15) or substitution with W (13.9) resulted in complete loss of activity; however, conversion of terminal carboxylate into an amide (13.20 & 13.21) resulted in moderate gain of activity of the peptide inhibitor. Substitution of aromatic residue, Y, with E (13.10) completely abolished the inhibitory potency of PCP-13.

Thus the structure of PCP-13 in D-configuration appears to consists of a N-terminal hydrophobic anchor spaced from the central HRD motif by a glycine residue possibly resulting in a turn conformation of the active peptide; Aromatic and hydrophobic interactions at the carboxy terminus may also add to the potency of PCP-13.

EXAMPLE IV

Testing PCP Peptides in Porcine Uterine Strip of Ex Vivo Basal Contraction Assay In ex vivo experiments using porcine uterine strips, the peptides were able to prevent both basal and $PGF_{2\alpha}$-induced contraction.

Uterine tissues from non-pregnant adult pigs were obtained from a local slaughter house and transported to the laboratory on ice. Uterine myometrial strips of approximately 1 cm in length were set up in organ baths containing Kreb's buffer equilibrated with 21% oxygen at 37° C. as we have described (Potvin, W. et al., 1990, *Br. J. Pharmacol.* 100:341–347; Varma, D. R. and Chemtob, S., 1993, *J. Pharmacol. Expt. Ther.* 265:1096–1104). Contractions were recorded by force transducers on Grass-polygraph. Strips were incubated with or without 100 µM peptides for 30 min before adding $PGF_{2\alpha}$ in step-wise increments ($10^{-9}$ to $10^{-6}$ M). Data were expressed as percentage increase over the basal level of average tension (g).

Figure 3A:
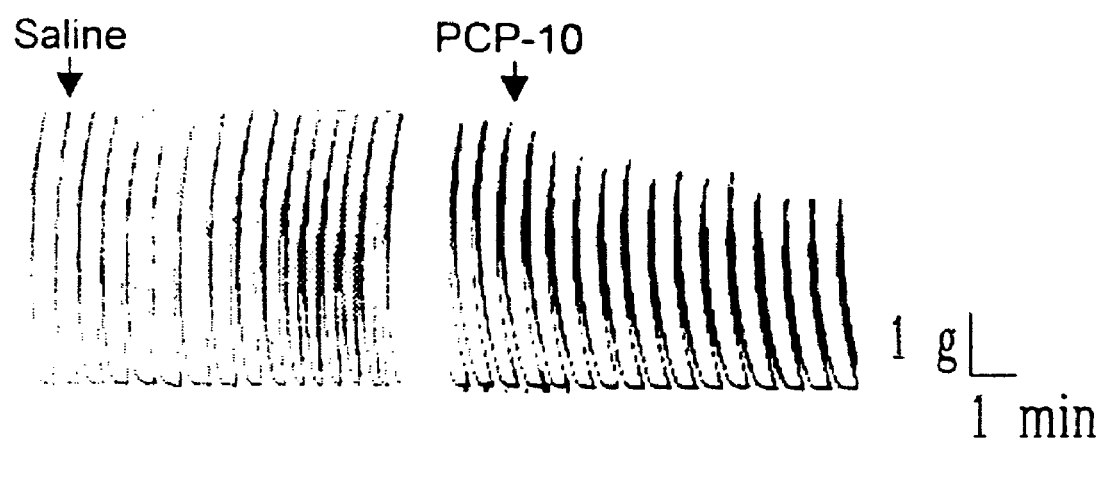
FIG. 3A illustrates the effects of PCP-10 upon spontaneous contractions of uterine smooth muscle.

A graph of spontaneous uterine contractions (known to be dependent upon prostanoids, mainly $PGF_{2\alpha}$) in the absence and the presence of 100 µM PCP-8 are shown in FIG. 3A. Addition of peptide to the strips reduced the force of basal contraction. A dose response of $PGF_{2\alpha}$ on uterine contractility in the presence or absence of PCP-8 and PCP-10 peptides is shown in FIG. 3B. More than 60% (PCP-8) and 80% (PCP-10) reduction in uterine contraction was observed in all concentrations of $PGF_{2\alpha}$ tested. Thus, both these peptides reduced spontaneous as well as $PGF_{2\alpha}$-induced contractions in the uterine strips.

EXAMPLE V

Testing PCP Peptides in Bovine Uterine Strip of Ex Vivo Basal Contraction Assay

Uterine tissues from non-pregnant adult bovine animals were obtained from a local slaughter house and transported to the laboratory on ice. Uterine myometrial strips of approximately 1 cm in length were set up in organ baths containing Kreb's buffer equilibrated with 21% oxygen at 37° C. as described above. Contractions were recorded on Grass-polygraph by force transducers. Strips were incubated with or without 100 µM peptides before adding $PGF_2$, in step-wise increments ($10^{-8}$ to $10^{-6}$ M). Data were expressed as change in basal level of average tension (g). The results are shown in FIG. 4. Application of PCP-10 peptide at 100 µM reversed the basal tone (contractile state) of the uterine muscle. Addition of $PGF_{2\alpha}$ up to 10 µM did not affect the relaxation produced by PCP-10 suggesting that the effects of PCP peptides are independent of the ligand, which was also shown in the previous results.

While the invention has been described in connection with specific embodiment thereof, it will be understood that it is capable of further modifications and this application is intended to cover any variations, uses or adaptations of the invention following in general, the principles of the invention and including such departures from the present disclosure as come within the known customary practice within the art to which the invention pertains and as may be applied to the essential features hereinbefore set forth, and as follows in the scope of the appended claims.

---

What is claimed is:

1. A prostaglandin F2 receptor antagonist consisting of an amino acid sequence derived from the second extracellular loop of a prostaglandin F2 receptor, said amino acid sequence consisting of one or more sequences selected from the group consisting of ilghrdyk (PCP-8; SEQ ID NO:1); ILGHRDYK (PCP-13; SEQ ID NO:13); ILAHRDYK (PCP-13.7, SEQ ID NO:4); ILGFRDYK (PCP-13.11; SEQ ID NO:5); ILGHKDYK (PCP-13.13; SEQ ID NO:6); ILGHRNYK (PCP-13.14; SEQ ID NO:7); ILGHQDYK (PCP-13.18; SEQ ID NO:8); ILGHRDY-amide (PCP-13.20; SEQ ID NO:9); ILGHRDYK-amide (PCP-13.21; SEQ ID NO:15); ILGWRDYK (PCP-13.22; SEQ ID NO:10); ILaHRDYK (PCP-13.8; SEQ ID NO:14); and ILGXRDYK (PCP-13.24; SEQ ID NO:11), wherein X is cyclohexyl alanine, and wherein small letters indicate L-amino acids and capital letters indicate D-amino acids.

2. A peptide consisting of a variant sequence of SEQ ID NO:1 in which one or two amino acid residues are substituted or deleted, wherein said variant sequence contains L- and/or D-amino acids and optionally, conversion of a C-terminal $CO_2H$ group to a $CONH_2$ group, and wherein said peptide is a prostaglandin F2 receptor antagonist.

3. A method for decreasing the likelihood of premature delivery of a fetus, which comprises the step of administering to a female in need of such treatment a therapeutically effective amount of the antagonist of claim 1.

4. A method for reducing the occurrence of and/or treating dysmenorrhea comprising the step of administering to a female in need of such treatment a therapeutically effective amount of the antagonist of claim 1.

5. A pharmaceutical composition comprising at least one antagonist of claim 1, and a pharmaceutically acceptable carrier.

6. A method for reducing uterine contraction comprising the step of administering to a female in need of such treatment a therapeutically effective amount of the antagonist of claim 1.

* * * * *

SEQUENCE LISTING

<160> NUMBER OF SEQ ID NOS: 15

<210> SEQ ID NO 1
<211> LENGTH: 8
<212> TYPE: PRT
<213> ORGANISM: artificial sequence
<220> FEATURE:
<223> OTHER INFORMATION: Peptide antagonist derived from the sequence of
      the Prostaglandin F2-alpha receptor.

<400> SEQUENCE: 1

Ile Leu Gly His Arg Asp Tyr Lys
1               5

<210> SEQ ID NO 2
<211> LENGTH: 8
<212> TYPE: PRT
<213> ORGANISM: artificial sequence -continued

```
<220> FEATURE:
<223> OTHER INFORMATION: Peptide antagonist derived from the sequence of
      the Prostaglandin F2-alpha receptor.

<400> SEQUENCE: 2

Trp Glu Asp Arg Phe Tyr Leu Leu
1               5

<210> SEQ ID NO 3
<211> LENGTH: 8
<212> TYPE: PRT
<213> ORGANISM: artificial sequence
<220> FEATURE:
<223> OTHER INFORMATION: Peptide antagonist derived from the sequence of
      the Prostaglandin F2-alpha receptor.
<220> FEATURE:
<221> NAME/KEY: SITE
<222> LOCATION: (1)..(8)
<223> OTHER INFORMATION: Peptide containing all D-amino acids.

<400> SEQUENCE: 3

Tyr Gln Asp Arg Phe Tyr Leu Leu
1               5

<210> SEQ ID NO 4
<211> LENGTH: 8
<212> TYPE: PRT
<213> ORGANISM: artificial sequence
<220> FEATURE:
<223> OTHER INFORMATION: Peptide antagonist derived from the sequence of
      the Prostaglandin F2-alpha receptor.
<220> FEATURE:
<221> NAME/KEY: SITE
<222> LOCATION: (1)..(8)
<223> OTHER INFORMATION: Peptide containing all D-amino acids.

<400> SEQUENCE: 4

Ile Leu Ala His Arg Asp Tyr Lys
1               5

<210> SEQ ID NO 5
<211> LENGTH: 8
<212> TYPE: PRT
<213> ORGANISM: artificial sequence
<220> FEATURE:
<223> OTHER INFORMATION: Peptide antagonist derived from the sequence of
      the Prostaglandin F2-alpha receptor.
<220> FEATURE:
<221> NAME/KEY: SITE
<222> LOCATION: (1)..(8)
<223> OTHER INFORMATION: Peptide containing all D-amino acids.

<400> SEQUENCE: 5

Ile Leu Gly Phe Arg Asp Tyr Lys
1               5

<210> SEQ ID NO 6
<211> LENGTH: 8
<212> TYPE: PRT
<213> ORGANISM: artificial sequence
<220> FEATURE:
<223> OTHER INFORMATION: Peptide antagonist derived from the sequence of
      the Prostaglandin F2-alpha receptor.
<220> FEATURE:
<221> NAME/KEY: SITE
<222> LOCATION: (1)..(8)
<223> OTHER INFORMATION: Peptide containing all D-amino acids.

<400> SEQUENCE: 6

Ile Leu Gly His Lys Asp Tyr Lys
```

-continued

```
<210> SEQ ID NO 7
<211> LENGTH: 8
<212> TYPE: PRT
<213> ORGANISM: artificial sequence
<220> FEATURE:
<223> OTHER INFORMATION: Peptide antagonist derived from the sequence of
      the Prostaglandin F2-alpha receptor.
<220> FEATURE:
<221> NAME/KEY: SITE
<222> LOCATION: (1)..(8)
<223> OTHER INFORMATION: Peptide containing all D-amino acids.

<400> SEQUENCE: 7

Ile Leu Gly His Arg Asn Tyr Lys
1               5

<210> SEQ ID NO 8
<211> LENGTH: 8
<212> TYPE: PRT
<213> ORGANISM: artificial sequence
<220> FEATURE:
<223> OTHER INFORMATION: Peptide antagonist derived from the sequence of
      the Prostaglandin F2-alpha receptor.
<220> FEATURE:
<221> NAME/KEY: SITE
<222> LOCATION: (1)..(8)
<223> OTHER INFORMATION: Peptide containing all D-amino acids.

<400> SEQUENCE: 8

Ile Leu Gly His Gln Asp Tyr Lys
1               5

<210> SEQ ID NO 9
<211> LENGTH: 7
<212> TYPE: PRT
<213> ORGANISM: artificial sequence
<220> FEATURE:
<223> OTHER INFORMATION: Peptide antagonist derived from the sequence of
      the Prostaglandin F2-alpha receptor.
<220> FEATURE:
<221> NAME/KEY: SITE
<222> LOCATION: (1)..(7)
<223> OTHER INFORMATION: Peptide containing all D-amino acids.
<220> FEATURE:
<221> NAME/KEY: Amidation
<222> LOCATION: (7)..(7)
<223> OTHER INFORMATION: The OH group of the Tyrosine at position 7 has
      been replaced with an NH2 group.

<400> SEQUENCE: 9

Ile Leu Gly His Arg Asp Tyr
1               5

<210> SEQ ID NO 10
<211> LENGTH: 8
<212> TYPE: PRT
<213> ORGANISM: artificial sequence
<220> FEATURE:
<223> OTHER INFORMATION: Peptide antagonist derived from the sequence of
      the Prostaglandin F2-alpha receptor.
<220> FEATURE:
<221> NAME/KEY: SITE
<222> LOCATION: (1)..(8)
<223> OTHER INFORMATION: Peptide containing all D-amino acids.

<400> SEQUENCE: 10

Ile Leu Gly Trp Arg Asp Tyr Lys
1               5
```

```
<210> SEQ ID NO 11
<211> LENGTH: 8
<212> TYPE: PRT
<213> ORGANISM: artificial sequence
<220> FEATURE:
<223> OTHER INFORMATION: Peptide antagonist derived from the sequence of
      the Prostaglandin F2-alpha receptor.
<220> FEATURE:
<221> NAME/KEY: SITE
<222> LOCATION: (1)..(8)
<223> OTHER INFORMATION: Peptide containing all D-amino acids.
<220> FEATURE:
<221> NAME/KEY: SITE
<222> LOCATION: (4)..(4)
<223> OTHER INFORMATION: Xaa= cyclohexyl alanine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 11

Ile Leu Gly Xaa Arg Asp Tyr Lys
1               5

<210> SEQ ID NO 12
<211> LENGTH: 8
<212> TYPE: PRT
<213> ORGANISM: artificial sequence
<220> FEATURE:
<223> OTHER INFORMATION: Peptide antagonist derived from the sequence of
      the Prostaglandin F2-alpha receptor.
<220> FEATURE:
<221> NAME/KEY: SITE
<222> LOCATION: (1)..(8)
<223> OTHER INFORMATION: Peptide containing all D-amino acids.

<400> SEQUENCE: 12

Ser Asn Val Leu Cys Ser Ile Phe
1               5

<210> SEQ ID NO 13
<211> LENGTH: 8
<212> TYPE: PRT
<213> ORGANISM: artificial sequence
<220> FEATURE:
<223> OTHER INFORMATION: Peptide antagonist derived from the sequence of
      the Prostaglandin F2-alpha receptor.
<220> FEATURE:
<221> NAME/KEY: SITE
<222> LOCATION: (1)..(8)
<223> OTHER INFORMATION: Peptide containing all D-amino acids.

<400> SEQUENCE: 13

Ile Leu Gly His Arg Asp Tyr Lys
1               5

<210> SEQ ID NO 14
<211> LENGTH: 8
<212> TYPE: PRT
<213> ORGANISM: artificial sequence
<220> FEATURE:
<223> OTHER INFORMATION: Peptide antagonist derived from the sequence of
      the Prostaglandin F2-alpha receptor.
<220> FEATURE:
<221> NAME/KEY: SITE
<222> LOCATION: (1)..(2)
<223> OTHER INFORMATION: The amino acids at positions 1 and 2 are
      D-amino acids.
<220> FEATURE:
<221> NAME/KEY: SITE
<222> LOCATION: (4)..(8)
<223> OTHER INFORMATION: The amino acids at positions 4 and 8 are
```

```
        D-amino acids.

<400> SEQUENCE: 14

Ile Leu Ala His Arg Asp Tyr Lys
1               5

<210> SEQ ID NO 15
<211> LENGTH: 8
<212> TYPE: PRT
<213> ORGANISM: artificial sequence
<220> FEATURE:
<223> OTHER INFORMATION: Peptide antagonist derived from the sequence of
      the Prostaglandin F2-alpha receptor.
<220> FEATURE:
<221> NAME/KEY: SITE
<222> LOCATION: (1)..(8)
<223> OTHER INFORMATION: Peptide containing all D-amino acids.
<220> FEATURE:
<221> NAME/KEY: Amidation
<222> LOCATION: (8)..(8)
<223> OTHER INFORMATION: The OH group of the Lysine at position 8 has
      been replaced with an NH2 group.

<400> SEQUENCE: 15

Ile Leu Gly His Arg Asp Tyr Lys
1               5
```